US010831996B2

(12) United States Patent
Torii et al.

(10) Patent No.: US 10,831,996 B2
(45) Date of Patent: Nov. 10, 2020

(54) INFORMATION PROCESSING APPARATUS, INFORMATION PROCESSING METHOD AND COMPUTER PROGRAM

(71) Applicant: TEIJIN LIMITED, Osaka (JP)

(72) Inventors: Kentaro Torii, Tokyo (JP); Chikashi Sugiura, Tokyo (JP); Shuichi Mitsuda, Tokyo (JP); Satoshi Aida, Tokyo (JP); Taro Ikezaki, Tokyo (JP)

(73) Assignee: TEIJIN LIMITED, Osaka (JP)

( * ) Notice: Subject to any disclaimer, the term of this patent is extended or adjusted under 35 U.S.C. 154(b) by 229 days.

(21) Appl. No.: 15/743,907

(22) PCT Filed: Jul. 13, 2016

(86) PCT No.: PCT/JP2016/070665
§ 371 (c)(1),
(2) Date: Jan. 11, 2018

(87) PCT Pub. No.: WO2017/010506
PCT Pub. Date: Jan. 19, 2017

(65) Prior Publication Data
US 2018/0203845 A1  Jul. 19, 2018

(30) Foreign Application Priority Data
Jul. 13, 2015 (JP) ................... 2015-140015

(51) Int. Cl.
G06F 40/268 (2020.01)
G06Q 50/22 (2018.01)
(Continued)

(52) U.S. Cl.
CPC ........... G06F 40/268 (2020.01); G06F 16/00 (2019.01); G06Q 50/22 (2013.01); G16H 10/60 (2018.01)

(58) Field of Classification Search
None
See application file for complete search history.

(56) References Cited

U.S. PATENT DOCUMENTS 5,371,807 A * 12/1994 Register ............... G06F 16/353
382/159
5,475,587 A * 12/1995 Anick ................... G06F 40/253
704/9

(Continued)

FOREIGN PATENT DOCUMENTS

JP  H0251765 A   2/1990
JP  H11203325 A  7/1999

(Continued)

OTHER PUBLICATIONS

Extended European Search Report for Application No. 16824486.1, dated Oct. 25, 2018.

(Continued)

Primary Examiner — Thuykhanh Le
(74) Attorney, Agent, or Firm — Marshall, Gerstein & Borun LLP

(57) ABSTRACT

A problem to be solved is to assist input of information by a user. An information processing device of one embodiment includes a keyword sequence generator generating a keyword sequence by performing morphological analysis on text data in natural language; a category information sequence generator acquiring category information corresponding to each keyword of the keyword sequence based on a database in which keywords are associated with category information and generating a category information sequence; the pattern extractor selecting a category information sequence pattern from category information sequence patterns according to correlation between the category information sequence and each category information sequence pattern; and a determiner comparing the (Continued)

selected category information sequence pattern with the category information sequence and generating presentation information according to a difference between the selected category information sequence pattern and the category information sequence.

17 Claims, 11 Drawing Sheets

(51) Int. Cl.
*G06F 16/00* (2019.01)
*G16H 10/60* (2018.01)

(56) References Cited

U.S. PATENT DOCUMENTS

| | | | | |
|---|---|---|---|---|
| 5,748,805 | A * | 5/1998 | Withgott | G06K 9/00469 382/306 |
| 5,799,268 | A * | 8/1998 | Boguraev | G06F 40/289 704/9 |
| 6,529,892 | B1 * | 3/2003 | Lambert | G06F 40/226 706/55 |
| 8,463,596 | B2 * | 6/2013 | Tsunokawa | G06F 16/36 704/10 |
| 8,600,735 | B2 * | 12/2013 | Dewulf | G06F 16/3329 704/9 |
| 8,620,658 | B2 * | 12/2013 | Nakade | G10L 15/30 704/257 |
| 2002/0002547 | A1 * | 1/2002 | Sako | G06F 40/289 704/9 |
| 2002/0010573 | A1 * | 1/2002 | Wakita | G06F 40/247 704/2 |
| 2002/0087357 | A1 * | 7/2002 | Singer | G06Q 50/24 705/2 |
| 2002/0120505 | A1 * | 8/2002 | Henkin | G06Q 30/02 705/14.69 |
| 2004/0215454 | A1 * | 10/2004 | Kobayashi | G10L 15/20 704/231 |
| 2006/0085181 | A1 * | 4/2006 | Komamura | G06F 16/93 704/9 |
| 2008/0288243 | A1 * | 11/2008 | Kobayashi | G06F 40/268 704/9 |
| 2009/0007018 | A1 * | 1/2009 | Ikeda | G06F 16/54 715/838 |
| 2009/0157650 | A1 * | 6/2009 | Chow | G06F 16/972 |
| 2009/0254348 | A1 * | 10/2009 | Moore | G10L 15/22 704/260 |
| 2009/0292528 | A1 * | 11/2009 | Kameyama | G10L 13/00 704/9 |
| 2010/0049499 | A1 * | 2/2010 | Hayashi | G06F 40/268 704/9 |
| 2010/0131277 | A1 * | 5/2010 | Nakano | G10L 15/22 704/270 |
| 2010/0179972 | A1 * | 7/2010 | Asano | H04N 21/4884 707/825 |
| 2011/0112835 | A1 * | 5/2011 | Shinnishi | G10L 15/18 704/235 |
| 2011/0161144 | A1 * | 6/2011 | Mizuguchi | G06Q 30/0241 705/14.4 |
| 2012/0136652 | A1 * | 5/2012 | Moyle | G06F 21/552 704/9 |
| 2012/0215523 | A1 * | 8/2012 | Inagaki | G06F 16/35 704/9 |
| 2012/0265575 | A1 * | 10/2012 | Torii | G06Q 10/06311 705/7.15 |
| 2012/0330662 | A1 | 12/2012 | Saikou | |
| 2013/0091116 | A1 * | 4/2013 | Kumar | G06F 16/951 707/708 |
| 2013/0103388 | A1 * | 4/2013 | Chen | G06F 40/194 704/9 |
| 2014/0189525 | A1 * | 7/2014 | Trevisiol | G06F 16/35 715/745 |
| 2014/0289323 | A1 | 9/2014 | Kutaragi et al. | |
| 2014/0365232 | A1 * | 12/2014 | Sadeghi | G06F 40/14 705/2 |
| 2015/0095356 | A1 * | 4/2015 | Wu | G06F 21/10 707/755 |
| 2015/0154956 | A1 * | 6/2015 | Brown | G06F 16/353 704/235 |
| 2015/0188879 | A1 * | 7/2015 | Cha | H04L 41/5035 709/223 |
| 2015/0227505 | A1 * | 8/2015 | Morimoto | G06F 40/30 704/9 |
| 2015/0242386 | A1 * | 8/2015 | Moreno Mengibar | G10L 15/08 704/235 |
| 2015/0347392 | A1 * | 12/2015 | Cavalin | G06F 40/284 704/9 |
| 2016/0147736 | A1 * | 5/2016 | Danielyan | G06K 9/00483 704/9 |
| 2017/0011742 | A1 * | 1/2017 | Jing | G01C 21/3608 |
| 2017/0103756 | A1 * | 4/2017 | Kobayashi | G10L 15/30 |
| 2018/0082344 | A1 * | 3/2018 | Sugawara | G10L 25/78 |

FOREIGN PATENT DOCUMENTS

| | | |
|---|---|---|
| JP | 2012-73739 A | 4/2012 |
| JP | 2012-226449 A | 11/2012 |
| JP | 2013-88906 A | 5/2013 |
| JP | 2014-182777 A | 9/2014 |
| WO | WO-2011/093025 A1 | 8/2011 |

OTHER PUBLICATIONS

International Application No. PCT/JP2016/070665, International Preliminary Report on Patentability, dated Jan. 25, 2018 (English Translation).

International Application No. PCT/JP2016/070665, International Search Report (Translation) and Written Opinion, dated Sep. 27, 2016.

European Patent Application No. 16824486.1, Communication Pursuant to Article 94(3) EPC, dated Apr. 25, 2019.

* cited by examiner

| STANDARD KEYWORD | KEYWORD |
|---|---|
| TAION | KT |
| TAION | BT |
| CHOSHOKU | BREAKFAST |
| CHOSHOKU | ASAGOHAN |
| CHOSHOKU | ASAMESHI |
| KYOHI | IIE |
| KYOHI | IYA |
| ... | ... |
| TOSHIBA TARO | TOSHIBA-SAN |
| TOSHIBA TARO | TOSHIBA-SAMA |
| ... | ... |

FIG. 3

| LARGE CATEGORY | SMALL CATEGORY | KEYWORD |
|---|---|---|
| LIVELIHOOD SUPPORT | MEAL | CHOSHOKU |
| LIVELIHOOD SUPPORT | MEAL | YUUSHOKU |
| STATE | WILL | IYOKU |
| STATE | WILL | KYOHI |
| MEASUREMENT | VITAL | TAION |
| MEASUREMENT | VITAL | KETSUATSU |
| ... | ... | ... |

FIG. 4

| ITEM ID | ITEM CONTENT | UNIT | EXPRESSION FORM 1 | EXPRESSION FORM 2 |
|---|---|---|---|---|
| ID_01 | BODY TEMPERATURE | °C | [NUMERICAL VALUE A] - [NUMERICAL VALUE B] | — |
| ID_02 | BLOOD PRESSURE | mmHg | [NUMERICAL VALUE A]~[NUMERICAL VALUE B] | [NUMERICAL VALUE A] |
| ID_03 | PULSE | bpm | [NUMERICAL VALUE A] | — |
| ID_04 | SpO2 | % | [NUMERICAL VALUE A] | — |
| ID_05 | WEIGHT | kg | [NUMERICAL VALUE A] | — |
| ... | ... | ... | ... | ... |

FIG. 12A

| ITEM ID | TEMPLATE | EXTRACTED DATA1 | EXTRACTED DATA2 |
|---|---|---|---|
| ID_01 | "TAION" [*2] [NUMERICAL VALUE A] "DO" [NUMERICAL VALUE B] "BU" | [NUMERICAL VALUE A] - [NUMERICAL VALUE B] | — |
| ID_01 | "TAION" [*2] [NUMERICAL VALUE A] " . " [NUMERICAL VALUE B] | [NUMERICAL VALUE A] - [NUMERICAL VALUE B] | — |
| ID_02 | "KETSUATSU" [*3] [NUMERICAL VALUE A] [*4] [NUMERICAL VALUE B] | [NUMERICAL VALUE A] | [NUMERICAL VALUE B] |
| ID_02 | "KETSUATSU" [*10] [NUMERICAL VALUE A] | [NUMERICAL VALUE A] | — |

FIG. 12B

| NUMERICAL VALUE | KANA | SIMILARITY |
|---|---|---|
| 80.0 | HACHIJYU, HACHIJYUTTENREI, HACHIJYUTTENZERO | 7 |
| 80.1 | HACHIJYUTTENICHI | 8 |
| ... | | |
| 99.4 | KYUUJYUUKYUUTENYON | 80 |
| 99.5 | KYUUJYUUKYUUTENGO | 97 |
| ... | — | |
| 100.0 | HYAKU, HYAKUTENREI, HYAKUTENZERO | 3 |

INFORMATION PROCESSING APPARATUS, INFORMATION PROCESSING METHOD AND COMPUTER PROGRAM

CROSS-REFERENCE TO RELATED APPLICATIONS

This application is the U.S. national phase of PCT Application No. PCT/JP2016/070665, filed on Jul. 13, 2016, which claims priority to Japanese Patent No. 2015-140015, filed on Jul. 13, 2015, the entire disclosures of which are hereby incorporated by reference in their entirety.

FIELD

Embodiments of the present invention relate to an information processing device, an information processing method and a computer program.

BACKGROUND

At the scene of home medical care, nursing care, or the like, staff of medical care and nursing care observe and diagnose states of patients and people who are cared for. The states of patients and people who are cared for are managed by the staff keeping a record of nursing care. For recording nursing care, it is necessary to fill out fixed items such as nursing care, a body temperature, a blood pressure, intake of food, and excretion.

To prevent omissions in the fixed items, it can be considered to provide an input form and check presence or non-presence of input and the input content. By this means, it is possible to promote the staff to input appropriate content without omissions in necessary items. At this time, it is convenient if input can be performed in a short period of time. While there is a method in which input is performed using a keyboard or a software keyboard in mobile equipment, or the like, such input is troublesome.

Meanwhile, in the case where fixed items are insufficient to recognize a state of a person in need of nursing care, a record of nursing care is also carried out by input of text in natural language. However, nursing care staff who has less knowledge or less experience sometimes does not enter necessary information or inputs information with terms other than standard terms. In this case, there is a problem that, even if the other person sees the record later, he/she cannot correctly recognize the state of the person in need of nursing care.

Further, in the both cases of filling out the fixed items and inputting of the text in natural language, when the staff is caring for the person, the staff often cannot secure time for keeping a record and for this reason, often keeps a record later from memory. In the case where the staff fills out the items later from memory, the staff sometimes forgets information to be recorded.

CITATION LIST

Patent Literature

[Patent Literature 1] Japanese Patent Laid-Open No. 2012-226449
[Patent Literature 2] Japanese Patent Laid-Open No. 2013-88906
[Patent Literature 3] Japanese Patent Laid-Open No. 2014-182777
[Patent Literature 4] Japanese Patent Laid-Open No. 2012-73739

Embodiments of the present invention are directed to assisting input of information by a user.

SUMMARY

According to one embodiment, an information processing device includes: a keyword sequence generator, a category information sequence generator, a pattern extractor and a determiner.

The keyword sequence generator generates a keyword sequence by performing morphological analysis on text data in natural language.

The category information sequence generator, based on a database including keywords and category information associated therewith, acquires category information corresponding to each keyword included in the keyword sequence and generates a category information sequence;

The pattern extractor selects a category information sequence pattern from a plurality of category information sequence patterns according to correlation between the category information sequence and each category information sequence pattern.

The determiner compares the selected category information sequence pattern with the category information sequence and generates presentation information according to a difference between the selected category information sequence pattern and the category information sequence.

BRIEF DESCRIPTION OF THE DRAWINGS

FIG. 3 is a diagram illustrating an example of a standard term database.

FIG. 4 is a diagram illustrating an example of a category information database.

FIGS. 12A and 12B each is a diagram illustrating an example of an item content database and a template database.

DETAILED DESCRIPTION

Embodiments of the present invention will be described below with reference to the drawings.

First Embodiment

Figure 1:
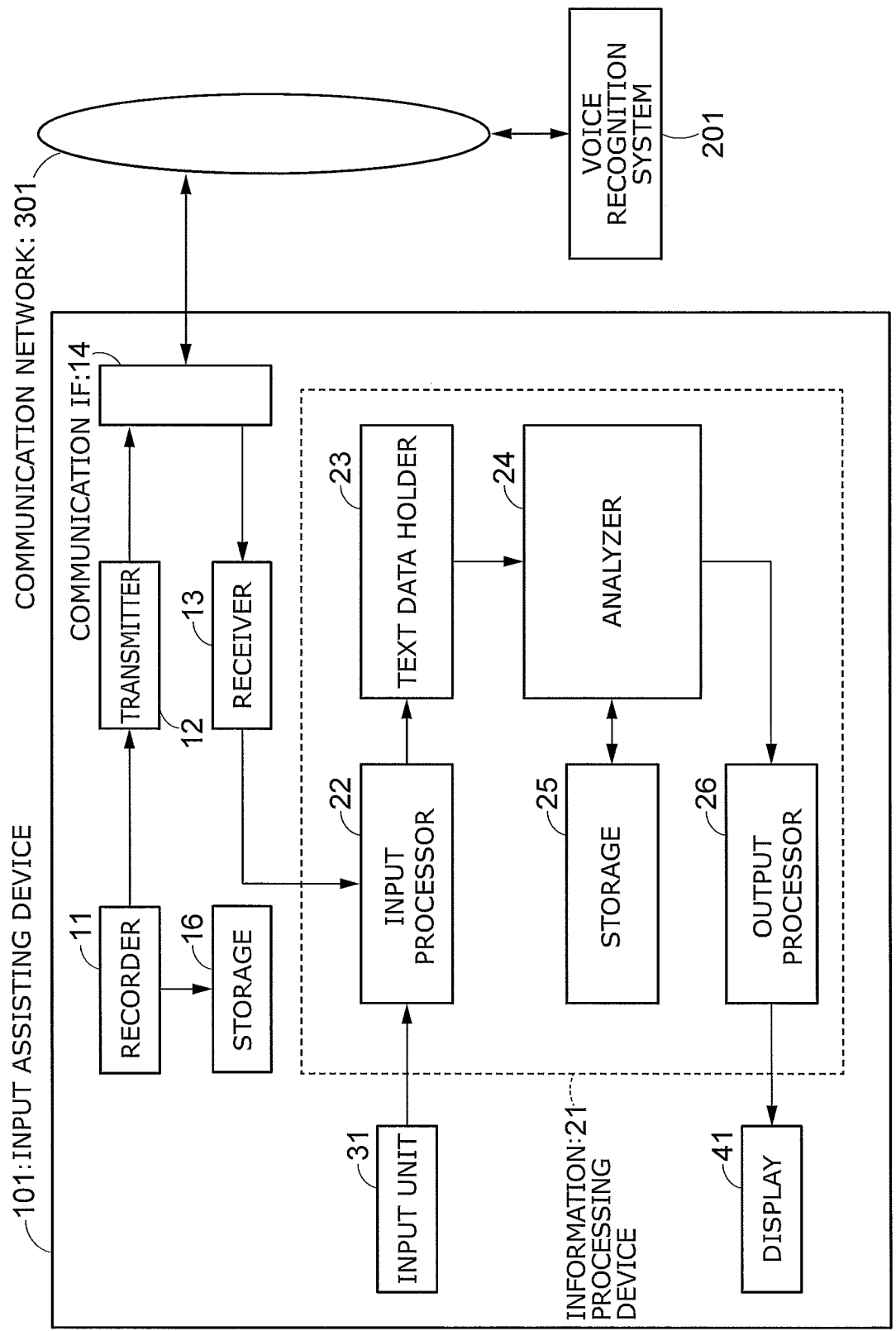
FIG. 1 is a diagram illustrating an input assisting device including an information processing device according to an embodiment of the present invention.

FIG. 1 illustrates an input assisting device according to an embodiment of the present invention. The input assisting device 101 is connected to a voice recognition system 201 via a network 301.

The input assisting device 101 includes a recorder (voice recorder) 11, a transmitter 12, a receiver 13, a communication interface (IF) 14, an information processing device 21, an input unit 31 and a display 41. The information processing device 21 includes an input processor 22, a text data holder 23, an analyzer 24, a storage 25 and an output processor 26.

The input assisting device 101 is a user terminal such as a smartphone, a mobile terminal, a tablet and a PC (Personal Computer). Functions of each processor provided at the input assisting device 101 can be implemented by utilizing a CPU, a memory, an auxiliary storage device, a communication device and an input/output interface typically provided at a computer device. Operation of each processor in FIG. 1 can be achieved by an operating system (OS) running on a processor such as a CPU and application running on the OS as an example. Particularly, there is a case where the application according to the present embodiment is referred to as managing application.

A microphone is provided at the input assisting device 101. A user such as staff of medical care and nursing care tweets information relating to a patient or a person who is cared for (record target person) to the microphone. The microphone picks up tweeted content (speech content), converts the tweeted content into an electric signal. The converted electrical signal is converted into voice digital data in a predetermined format at a processing circuit including an AD converting circuit (not illustrated) and input to the recorder 11. Note that the microphone may be incorporated into the input assisting device 101 or may be connected to the input assisting device 101 from outside via an external interface.

The recorder 11 acquires the voice digital data of the tweet from the microphone and outputs the voice digital data to the transmitter 12. Further, the recorder 11 creates a voice file in a format determined in advance by adding a file header, or the like, to the voice digital data. A format of the voice file may be arbitrary. As an example, it is possible to use a WAVE (RIFF waveform Audio Format) format, a PCM (Pulse Code Modulation) format, an mp3 format, or the like. The recorder 11 stores the created voice file in the storage 16. The storage 16 may be managed by, for example, a file system mounted on the OS. The storage 16 is formed with an arbitrary storage medium such as a hard disk, an SSD and a memory. The memory may be a non-volatile memory such as an SRAM and a DRAM or a non-volatile memory such as a NAND and an MRAM. By the voice file being stored in the storage 16, it is possible to read out and reproduce the voice file later or perform voice recognition.

The transmitter 12 communicates with a voice recognition system 201 on a communication network 301 via the communication interface 14 based on predetermined communication protocol. While arbitrary communication protocol can be used as communication protocol processed by the transmitter 12, for example, TCP (or UDP)/IP can be used. Alternatively, it is also possible to utilize protocol based on TCP (or UDP)/IP, for example, http.

The transmitter 12 generates a voice recognition request for requesting voice recognition of voice digital data to the voice recognition system 201 based on the voice digital data received from the recorder 11. A header, or the like, which is necessary for the above-described protocol for voice recognition may be added to the voice digital data. The voice recognition request is generated according to protocol for voice recognition processed by the voice recognition system 201. The transmitter 12 transmits the generated voice recognition request to the voice recognition system 201 via the communication interface 14 and the communication network 301.

The communication interface 14, which is an interface for connecting to the communication network 301, may be a wireless interface or a wired interface. In the case of the wireless interface, for example, the communication interface 14 includes a communication circuit for wireless communication (such as an integrated circuit) and an antenna. In the case of the wired interface, the communication interface 14 includes a communication circuit for wired communication, a connection port for a communication cable, or the like. The communication network 301 may be a wireless network, a wired network, or a network of combination thereof. As an example, the communication network 301 may be a network including the Internet.

The voice recognition system 201 receives the voice recognition request transmitted from the input assisting device 101 via the communication network 301. The voice recognition system 201 extracts the voice digital data from the voice recognition request and performs voice recognition processing on the voice digital data to convert the voice digital data into text data. The text data is data of an arbitrary character string (text) in natural language. The voice recognition system 201 transmits a voice recognition response including the text data acquired through conversion to the input assisting device 101 via the communication network 301. Note that the voice recognition system 201 may be provided inside the input assisting device 101 instead of being provided on the communication network 301.

The receiver 13 communicates with the voice recognition system 201 on the communication network 301 via the communication interface 14 based on predetermined communication protocol in a similar manner to the transmitter 12. The receiver 13 receives the voice recognition response transmitted from the voice recognition system 201 via the communication network 301 and the communication interface 14. The receiver 13 extracts text data from the received voice recognition response and passes the text data to the input processor 22 of the information processing device 21.

The input processor 22 passes the text data passed from the receiver 13 to the text data holder 23. The text data holder 23 stores the text data passed from the input processor 22 inside the text data holder 23. The text data holder 23 may be a memory or a device such as an SSD and a hard disk. In the case of a memory, the text data holder 23 may be a volatile memory such as an SRAM and a DRAM or a non-volatile memory such as a NAND and an MRAM. The text data holder 23 may be part of the storage 16 or part of the storage 25.

The input unit 31 is an input interface which allows the user to input various kinds of instructions or data. The input unit 31 may be, for example, a keyboard, a touch panel, a mouse, or the like, or may be a voice input unit which utilizes the above-described microphone. The input processor 22 may update the text data held in the text data holder 23 based on the data input at the input unit 31. For example, the input processor 22 may change part of the text data to other characters, numerical values, or the like, delete part of the text data or add new characters, numerical values, or the like.

The analyzer 24 reads out the text data held in the text data holder 23 and performs analyzing processing on the text data. Note that, while, in the present embodiment, a case is described where text data obtained through voice recognition is subjected to analyzing processing, analyzing processing may be performed on text data input by the user through a keyboard, or the like.

The analyzer 24 includes a keyword sequence generator 56, a standard term detector 52, a category information sequence generator 53, a pattern extractor 54 and a determiner 55. The keyword sequence generator 56 includes a morphological analyzer 51 and a standard term detector 52.

The analyzer 24 is connected to the storage 25, and various kinds of databases (DBs) to be used in processing at the analyzer 24 are stored in the storage 25. For example, a standard term database 61, a category information database 62 and a category information sequence pattern database 63 which will be described later are stored in the storage 25.

The morphological analyzer 51 at the analyzer 24 performs morphological analysis on the text data. The morphological analysis is dividing a sentence into morphemes which are character strings of minimum unit having a meaning and then classifying the divided character strings into word classes (a pronoun, a particle, a general noun, a linking particle, a proper noun, a verb, an adjective, or the like). A keyword sequence (input keyword sequence), which is formed with a plurality of keywords, can be obtained from the text data through the morphological analysis. Each of the keywords is a character string obtained through the morphological analysis. Character strings meaning a particle, a verbal auxiliary, a conjunction, a mark (such as a point and a punctuation mark), or the like, may be dealt as keywords. For example, if "iyokutekini shokujiwosare, zenryou shesshusaremashita." is divided into morphemes, "iyoku (noun, general)", "teki (noun, suffix)", "ni (particle, made adverb)", "shokuji (noun, conjugation of line sa)", "wo (particle, case particle)", "sa (verb, independence)", "re (verb, suffix)", ", (mark, punctuation)", "zenryou (noun, general)", "sesshu (noun, conjugation of line sa)", "sa (verb, independence)", "re (verb, suffix)", "mashi (verbal auxiliary)", "ta (verbal auxiliary)" and ". (mark, point)".

The standard term database (standard term DB) 54 holds keywords which are standard (standard keywords) and non-standard keywords in association with each other. The non-standard keywords have expression different from expression of the standard keywords but have the same meaning as the standard keywords. For example, a case is assumed where nursing care staff tweets "taion" or "BT" (Body Temperature) in the same meaning as "KT" (Korper Temperature). Among a plurality of terms indicating the same meaning in this manner, one term is registered as a standard keyword and other terms are registered as non-standard keywords. An example of the standard term database 54 is illustrated in FIG. 3. In the case of this example, "taion" is registered as the standard keyword, and "KT" and "BT" are registered as non-standards keywords. Further, "choshoku" is registered as the standard keyword, and "asagohan", "asameshi" and "breakfast" are registered as non-standard keywords. The standard keyword may be arbitrarily selected, and, for example, it is also possible to register "KT" as the standard keyword, and register "taion" and "BT" as non-standard keywords. Alternatively, it is also possible to register "BT" as the standard keyword and register "taion" and "KT" as non-standard keywords. Further, standard keywords and non-standard keywords relating to name of patients and people who are cared for (record target people) may be registered. In the example in FIG. 3, "Taro Toshiba" is registered as the standard keyword, and "Toshiba-san" and "Toshiba-sama" are registered as non-standard keywords. The standard terms and non-standard terms relating to name of patients and people who are cared for (record target people) may be managed in a different database.

The standard term detector 52 is connected to the morphological analyzer 51 and the storage 25. The standard term detector 52 causes all the keywords in the input keyword sequence obtained by the morphological analyzer 51 to be uniformly expressed with standard keywords. Specifically, the standard term detector 52 detects a keyword which does not match a standard keyword based on the standard term database 54 within the storage 25 for each keyword in the input keyword sequence, and replaces the detected keyword with the standard keyword. For example, in the case where "BT" is included in the input keyword sequence, "BT" is replaced with "taion". The keyword sequence in which keywords have been uniformly expressed with standard keywords is sometimes referred to as a standard keyword sequence. Note that keywords relating to a particle, a verbal auxiliary, a conjunction, or the like, may be deleted from the input keyword sequence. In this case, deletion processing may be performed at the morphological analyzer 51. Alternatively, in the case where keywords relating to a particle, a verbal auxiliary, a conjunction, or the like, are also registered in the standard term database 54, the keywords may be set as targets to be replaced with standard keywords.

The category information database (category information DB) 55 holds categories such as a large category and a small category for each standard keyword. An example of the category database 55 is illustrated in FIG. 4. For example, a large category of a standard keyword "choshoku" is "livelihood support", and a small category is "meal". Further, a large category of a standard keyword "taion" is "measurement", and a small category is "vital". The number of categories is not limited to two, and there may be one or three or more categories.

The category information sequence generator 53 is connected to the standard term detector 52 and the storage 25. The category information sequence generator 53 searches the category information database 55 for each keyword of the keyword sequence (standard keyword sequence) obtained by the standard term detector 52. If the corresponding keyword exists, the category information sequence generator 53 extracts category information (here, a large category and a small category) of the keyword from a column of the large category sequence and a column of the small category. If keywords relating to a particle, a verbal auxiliary, a conjunction, or the like, do not exist in the category information DB 55, such word classes may be not considered as a search target. Concerning terms relating to a numeral and an amount, the category information database 62 is not searched, and category information may be determined as predetermined category information such as "numerical value" or "amount". There may be word classes other than a numeral, or the like, which is determined as specific category information without searching the category information database 62. In this manner, by acquiring category information of each keyword of the keyword sequence obtained by the standard term detector 52 and arranging the category information in order of corresponding keywords, it is possible to obtain a category information sequence.

For example, the keyword sequence includes three keywords, and, if the first keyword is "choshoku", because the large category and the small category are respectively "livelihood support" and "meal", "livelihood support" and "meal" can be respectively obtained as category information. Note that the large category and the small category may be collectively regarded as one piece of category information. For example, "livelihood support, meal" may be dealt as one piece of category information.

If the second keyword is "100" which is a numeral, "numerical value" can be obtained as the category information. If the third keyword is "kyohi", because the large category and the small category are respectively "state" and "will", "state" and "will" can be respectively obtained as the category information. Therefore, "livelihood support", "meal", "numerical value", "state" and "will" can be obtained as the category information sequence.

Note that it is assumed in this example that keywords relating to a particle, a verbal auxiliary, a conjunction, or the like, are excluded from the keyword sequence in advance or excluded from a search target, or not registered in the category information database.

Figures 5, 6:
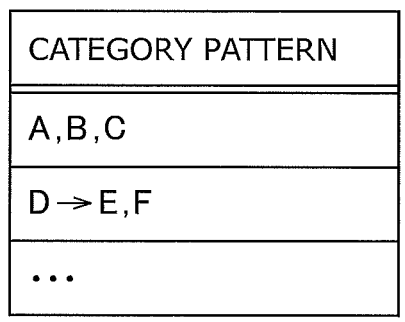
FIG. 5 is a diagram illustrating an example of a category information sequence pattern database.
FIG. 6 is a diagram illustrating an example of a nursing care record input screen.

The pattern database (pattern DB) 63 holds a plurality of category information sequence patterns. The category information sequence pattern is combination of a plurality of pieces of category information, and may include information relating to order of the category information. An example of the pattern database 63 is illustrated in FIG. 5. The category information sequence pattern "A, B, C" includes A, B and C as category information. A, B and C are abstracted category information, and, actually, are specific values such as "livelihood support", "state", "vital" and "numerical value" as mentioned above. Alternatively, the large category and the small category may be collectively regarded as one piece of category information, and A may express bound category information of "livelihood, meal". The category information sequence pattern "A, B, C" does not include constraint relating to order among category information A, B and C. A category information sequence pattern "D→E, F" includes D, E and F as category information, and includes constraint of order between D and E that E has to appear after D. Here, D, E and F are abstracted category information, and, actually, are specific values such as "livelihood support", "state", "vital" and "numerical value" as mentioned above.

Figure 2:
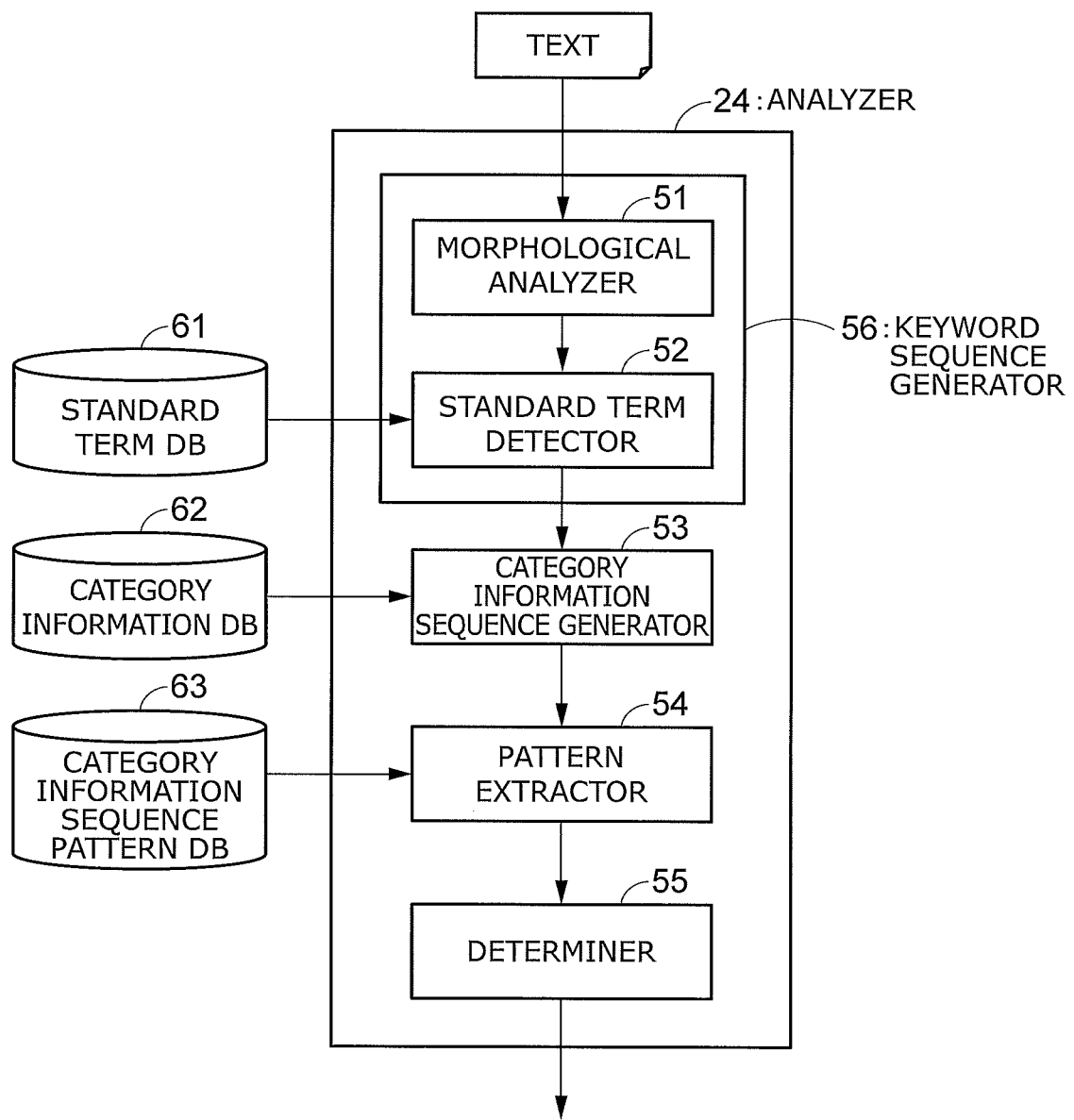
FIG. 2 is a functional block diagram of an analyzer in the information processing device in FIG. 1.

While, in FIG. 2, the standard term database 61 and the category information database 62 are separately provided, these may be integrated into one common database. In this case, the standard term detector 52 and the category information sequence generator 53 only have to access the common database.

The pattern extractor 54 is connected to the category information sequence generator 53 and the storage 25. The pattern extractor 54 selects a category information sequence pattern with high correlation from the category information sequence pattern database 63 according to correlation between the category information sequence obtained by the category information sequence generator 53 and each category information sequence pattern held in the category information sequence pattern database 63. For example, the pattern extractor 54 calculates a similarity between the category information sequence and each category information sequence pattern and selects a category information sequence pattern from the category information sequence pattern database 63 based on the calculated similarity. The similarity can be calculated using a Jaccard coefficient for quantifying a similarity between two sets, cosine similarity for quantifying a similarity of a vector, or the like. Alternatively, it is possible to use a method for quantifying a similarity between character strings (a degree of difference or a degree of overlap). For example, it is possible to use a minimum edit distance or a Levenshtein distance as a similarity between two character strings. There can be a case where a similarity is higher as a value is smaller or a case where a similarity is higher as a value is greater depending on definition of the similarity.

An example of evaluating a similarity between the category information sequence and the category information sequence pattern using a Jaccard coefficient for calculating a similarity between sets will be described. For example, in the case where the category information sequence X="A, B, C", and the category information sequence pattern Y="A, B, D", the Jaccard coefficient can be calculated with $$\frac{|X \cap Y|}{|Y \cup X|} \qquad \text{[EXPRESSION 1]}$$

where "X∩Y" is a common set of sets X and Y, "X∪Y" is a sum set of sets X and Y, and |S| indicates the number of elements of a set S.

In the case of the above example, because "X∩Y"={A, B}, and "X∪Y"={A, B, C, D}, the Jaccard coefficient of X and Y is 2/4=0.5. In the case of another category information sequence pattern Z="A, D, E", because "X∩Z"={A}, and "X∪Z"={A, B, C, D, E}, the Jaccard coefficient of X and Z is 1/5=0.2. In the case of this example, Y has a larger similarity with X than Z.

Further, in the case where there is constraint of order of constituent elements like D→E in the category information sequence pattern, it is checked whether order of constituent elements of the category information sequence (appearance order in the above-described morphological analysis result) satisfies the constraint of order of the constituent elements of the category information sequence pattern, and in the case where the constraint is not satisfied, a Jaccard coefficient with the category information sequence pattern is not calculated, and the processing is skipped. Alternatively, a Jaccard coefficient may be calculated while a flag indicating that constraint is violated is held for the category information sequence pattern.

Meanwhile, in the case where a similarity between the category information sequence and the category information sequence pattern is evaluated using a method for calculating a similarity between character strings, a similarity between the character strings may be calculated while the category information sequence and the category information sequence pattern are each regarded as a character string in which a plurality of pieces of category information included in them are bound in this order. At this time, for example, in the case of the category information sequence pattern "A, B, C", it is possible to calculate similarities between six patterns of ABC, ACB, BAC, BCA, CAB and CBA, and a character string indicating the category information sequence are calculated, and set the highest similarity as the similarity between the category information sequence and the category information sequence pattern. In the case of the category information sequence pattern "D→E, F", because order of EF is fixed, it is possible to calculate similarities between two patterns of DEF and FDE and the character string of the category information sequence and employ the highest similarity as the similarity between the category information sequence and the category information sequence pattern.

As described above, it is only necessary to select a category information sequence pattern which satisfies a predetermined condition with the category information sequence among all the category information sequence patterns. The predetermined condition is, for example, that a category information sequence pattern having the highest similarity is selected, that a category information sequence pattern having a value indicating a similarity equal to or less than a threshold (or equal to or greater than a threshold) is selected, that a category information sequence pattern having a value indicating a similarity falling within a certain range is selected, or the like. Alternatively, the predetermined condition may include that constraint relating to order of constituent elements in the pattern is not violated. The pattern extractor 54 transmits the selected category information sequence pattern and the category information sequence of the input text (category information sequence obtained at the category information sequence generator 53) to the determiner 55.

The determiner 55 compares the category information sequence pattern selected at the pattern extractor 54 with the category information sequence of the input text and generates presentation information according to a difference between them. For example, the determiner 55 generates presentation information which specifies a lacking element not included in the category information sequence of the input text among elements of the category information sequence pattern. Alternatively, the determiner 55 may generate a message indicating that the input text lacks a keyword relating to the lacking element as the presentation information. The output processor 26 receives the presentation information generated by the determiner 27 and outputs a signal displaying the presentation information to the display 41.

For example, it is assumed that, as a result of comparison between the category information sequence and the category information sequence pattern, the determiner 55 determines that "numerical value" is included in the category information sequence pattern, but not included in the category information sequence of the input text, and all the other elements are commonly included in both the category information sequence pattern and the category information sequence of the input text. In this case, the determiner 55 may specify "numerical value" included in the category information sequence pattern and generate a message such as "input lacks a keyword relating to "numerical value"". Further, in the case where "vital" is included in the category information sequence pattern, but not included in the category information sequence of the input text, the determiner 55 may generate a message such as "input lacks a keyword relating to "vital"".

In the case where there exists an element which is not included in the category information sequence pattern but included in the category information sequence of the input text, the determiner 55 may generate a message indicating that the element does not exist in the category information sequence pattern. For example, in the case where "state" and "will" do not exist in the category information sequence pattern, but exists in the category information sequence of the input text, the determiner 55 may generate a message such as "category information of "state" and "will" does not exist in the category information sequence pattern". Alternatively, the determiner 55 may specify a keyword which becomes a basis of the category information of "state" and "will" from the input text and may generate a message indicating that the category information relating to the specified keyword does not exist in the category information sequence pattern. For example, in the case where a keyword which is a basis of the category information of the above-described "state" and "will" is "iyoku", the determiner 55 may generate a message such as "category information relating to the keyword "iyoku" does not exist in the category information sequence pattern". By presenting such a message to the user, it is possible to review the category information sequence pattern database and further improve accuracy.

While, in the above description, a lack in the category information sequence is presented to staff when the staff inputs a record of nursing care, the lack in the category information sequence does not have to be presented when the staff inputs a record of nursing care and may be presented only to specific staff such as a manager. For example, by confirming whether or not there is a lack in the category information sequence for the record of nursing care input by nursing care staff for a certain period of time and presenting a list of lacking nursing care records and the category information sequences to the manager, it is possible to coach staff who inputs the nursing care record as to input content of the nursing care record individually or it is possible to present an element which is likely to be lacked in the nursing care record during orientation for new staff. Further, in the nursing care record for each staff, by counting category information sequences in which there are lacking elements, per each element in the category information sequences or per lacking element, it is possible to coach the staff as to what kind of element is likely to be lacked in what kind of record. Further, by performing the above-described analysis for each attribute of staff (job type, years of experience, years of the post), it is possible to make use of the analysis to coaching of the nursing care record according to attributes of the staff.

The standard term detector 52 may calculate the number of keywords which are non-standard terms among the input text. By dividing the number by the total number of keywords of the input text, it is possible to calculate a use rate of the standard keyword in the input text. For example, an average value of the standard keyword use rate in the nursing care record may be calculated for each staff.

In the case where, for the category information sequence of a certain input text, a category information sequence pattern for which a Jaccard coefficient is 1 does not exist and the category information sequence is not part of any category information sequence pattern, because the category information sequence does not match any category information sequence pattern in the category information sequence pattern database, it can be considered that the category information sequence has a new category information sequence pattern. It is also possible to inquire about whether such a category information sequence is registered in the category information sequence pattern database as a category information sequence pattern to the user when the user inputs the nursing care record. Alternatively, it is also possible to present this procedure only to specific staff such as a manager without presenting the procedure the staff when the staff inputs the nursing care record. For example, it is only necessary to extract category information sequences which become candidates for a new category information sequence pattern from category information sequences for the nursing care records input by the staffs in a predetermined period of time, present the category information sequences to a manager along with appearance frequencies thereof, and the manager only has to select a category information sequence to be made a category information sequence pattern from the category information sequences and register the selected category information sequence in the category information sequence pattern database.

The display 41 is an arbitrary device such as a liquid crystal display panel, an organic EL and an electronic ink display device, which displays an image, data, or the like. The display 41 displays text data which is a processing target at the analyzer 24 on a screen. Further, the display 41 displays presentation information (such as a message) on a screen based on a signal passed from the output processor 26. The user can confirm whether or not the text lacks necessary items, or the like, by confirming the message and the text displayed on the screen. For example, if the displayed message is "input lacks a keyword relating to "numerical value"", the user may confirm whether the displayed text lacks a necessary numerical value and, if the text lacks a necessary numerical value, may input the necessary numerical value using the input unit 31. For example, if the displayed text is "taion wa seijyou", the user may determine that the text lacks in a measurement value of the body temperature and may update (correct) the text to such as "taion wa 36 dode seijyou". The user may give an instruction to perform processing by the analyzer 24 again on the updated text from the input unit 31 so that processing at the analyzer 24, or the like, is repeated in a similar manner as described above.

When the user confirms that there is no problem in content of the displayed text or the updated text, the user may input an instruction of storing the text, and the information processing device 21 may store the text data in the storage 25 or another storage device in response to the instruction of storing the text. The stored text data may be managed by application, and the text data may be read out by an instruction of browsing from the input unit 31 and may be displayed at the display 41. The application may manage the accumulated text data as tweeted messages and may manage the tweeted messages in chronological order for each patient and person who is cared for (record target person) who is a target for tweeting. The patient or the person who is cared for may be input and specified by the user through the input unit 31, or, in the case where information (such as name) of the patient or the person who is cared for is included in the text data, by the information being compared with a list of patients and people who are cared for, and, if matched information (such as name) exists, the patient or the person who is cared for may be extracted from the matched information and specified.

A specific example of the present embodiment will be described below. A case will be described as an example where the user tweets and a value in each input item of the form of a nursing care record input screen is automatically input with use of the text data obtained through voice recognition. FIG. 6 illustrates an example of the form of the nursing care record input screen. Note that, while, in FIG. 6, a value has already been input in each item, it is assumed that a value is not input in each item before processing, and any of various kinds of buttons are not selected.

It is assumed that the text data tweeted by the user and obtained through voice recognition is "Toshiba-san no hainyou kakunin shimashita. Tokuni ijyounaku, ryoumofutsuudeshita". Note that it is assumed that the tweeted content of the user matches the content of this text data, and there is no error in voice recognition. It is assumed that morphological analysis is performed on the text data to acquire an input keyword sequence, and further, standard term detection is performed, and a standard keyword sequence "Toshiba Taro", "hainyou", "kakunin", "ijyou", "nai", "ryou" and "futsuu" is obtained. Keywords of a word class of a particle, or the like, are excluded. It is assumed that "Toshiba Taro" is registered as a standard keyword in the standard term database, and "Toshiba-san", or the like, is registered as a non-standard keyword (see FIG. 3).

The list of patients and people who are cared for (lists of record target people) are stored in the storage 25, and personal information (such as name) of patients and people who are cared for is stored in this list. Because "Toshiba Taro" of the standard keyword sequence matches an item of "name" in this list, "Toshiba Taro" is automatically set in an item 91 of "record target person" on the nursing care record input screen. That is, a keyword relating to the item 91 (keyword relating to name) on the input screen is specified from the standard keyword sequence, and information (here, "Toshiba Taro") according to the keyword is set as a value of the item 91.

Further, a list of diagnosis observation items is stored in the storage 25, and various kinds of diagnosis and observation items (items for measurement) are stored in this list. For example, there can be items such as "urination", "body temperature", "blood pressure", "dietary intake" and "passage". Because "hainyou" in the standard keyword sequence matches this list, "urination" is set at an item 92 of "nursing care record content" on the nursing care record input screen. This processing is performed at the analyzer 24. That is, a keyword relating to the item 92 on the input screen (keyword relating to an item for measurement) is specified from the standard keyword sequence, and information according to the keyword (here, "urination") is set as a value of the item 91. Further, a keyword "kakunin" located within certain characters from "hainyou" in the standard keyword sequence is associated with a "Yes" button 93 on the nursing care record input screen, and the "Yes" button 93 is emphasized ("Yes" means that there is urination). That is, the "Yes" button on the nursing care record input screen is associated with a keyword of "kakunin" in advance by managing application of the nursing care record input screen, and the keyword of "kakunin" in the standard keyword sequence is associated with the "Yes" button 93 according to this association in advance. Note that a term other than "kakunin" may be further associated with the "Yes" button 93. Note that an "abnormality" button is, for example, associated with keywords of "ijyou" and "ari", and if these keywords exist within certain characters after "hainyou" and if the number of characters between "ijyou" and "ari" is within a certain value, the "abnormality" button can be selected and can be emphasized. In a similar manner, "futsuu" which exists within certain characters after the keyword "ryou" located after "hainyou" in the standard keyword sequence is specified, this keyword is associated with a "normal" button 94 on the nursing care record input screen, and the "normal" button 94 is emphasized. That is, a "large quantity" button, the "normal" button and a "small quantity" button on the nursing care record input screen are associated with keywords such as "ooi", "futsuu", "sukunai", or the like, in advance by the managing application of the nursing care record input screen. Note that setting of items and selection of buttons described here can be realized by performing processing based on a template in a second embodiment which will be described later. Further, of course, it is also possible to use methods other than the method described here.

Further, the category information database 62 is searched by the category information sequence generator 53 based on the standard keyword sequence. The matched keywords are, for example, "hainyou", "ijyou", "nai", "ryou" and "futsuu", and a category information sequence pattern with the highest similarity with the category information sequence obtained from these is specified from the category information sequence pattern database. Here, it is assumed that all the elements are common between the category information sequence and the specified category information sequence pattern. Therefore, it is determined that there is no particular insufficient item, and a message such as lack of an item does not have to be displayed. In a form 95 at a lower side on the nursing care record input screen, the text data obtained through voice recognition is stored. By a register button 97 being selected, data of each item and data in a form on the nursing care record input screen are stored in the storage 25 or another storage device as nursing care record data. The nursing care record data may be managed in chronological order for each record target person (patient and a person who is cared for) by the managing application after information such as date and time being added.

Figures 7, 8:
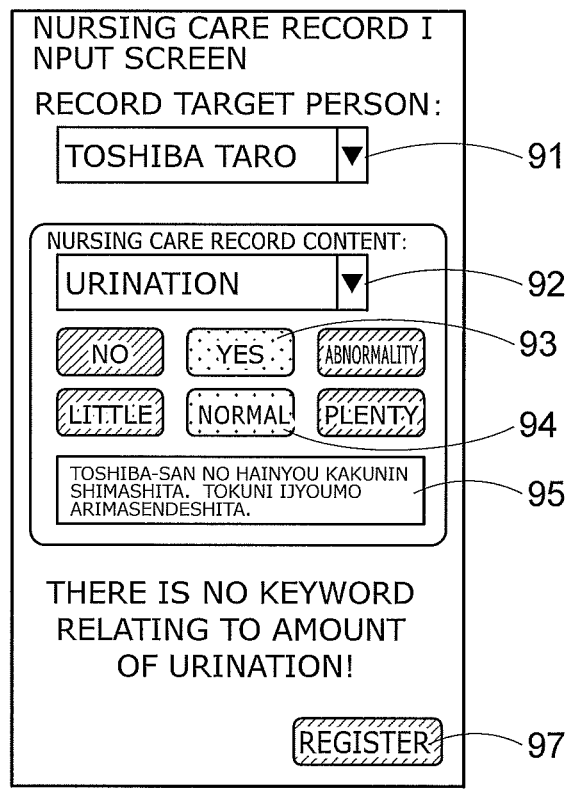
FIG. 7 is a diagram illustrating another display example of the nursing care record input screen.
FIG. 8 is a diagram illustrating another form of the nursing care record input screen.

Here, it is assumed that there is no content relating to the amount of urination in content tweeted by the user and the standard keyword sequence is "Toshiba Taro", "hainyou", "kakunin", "ijyou" and "nai". This standard keyword sequence is different from the example described above in that "ryou" and "futsuu" do not exist. In this case, as illustrated in FIG. 7, the "normal" button 94 is not selected (not emphasized) on the nursing care record input screen. In the form 95 at the lower side in FIG. 7, the text data obtained through voice recognition relating to tweet this time is displayed. This time, it is assumed that it is determined that, for example, an element (category information) relating to an amount does not exist in a category information sequence between the category information sequence obtained based on the standard keyword sequence and a category information sequence pattern which is the most similar to the category information sequence. Therefore, a message 96 such as "a keyword relating to an amount of urination does not exist" may be displayed on the nursing care record input screen. Alternatively, the message may be displayed in other forms such as pop-up. A user who sees this message 96 confirms the nursing care record input screen and determines that he/she has forgot tweeting an amount of urination. Therefore, the user may manually select the "normal" button 94 using the input unit 31. Alternatively, the user may correct the text data within the form 95 using the input unit 31. For example, if the amount of urination is normal, it can be considered that the text data can be corrected to a sentence similar to the form in FIG. 6. The corrected text data is updated through the input processor 22 in the text data holder 23. After the user confirms that there is no problem in the updated content, the user selects the register button 97, so that updated data of each item and in the form is stored as the nursing care record data.

FIG. 8 illustrates an example of another form of the nursing care record input screen. While, in the above-described example, voice recognition and analysis processing are performed every time the user tweets, and the nursing care record input screen as illustrated in FIG. 6 or FIG. 7 is displayed. In the present example, nursing care record data is generated for each tweet of the user, information such as date and time is added, and the nursing care record data is sequentially stored in the storage 26 or another storage device. The nursing care record input screen is not displayed for each tweet of the user. When the user requests display of a list of the nursing care record data through the managing application, the list of the nursing care record data as illustrated in FIG. 8 is displayed at the display 41. This list includes an entry of the nursing care record data which is not confirmed (approved) by the user. A value of each item on the nursing care record input screen illustrated in FIG. 6 or FIG. 7 is simply displayed in each entry. After it is confirmed that information is completely input in each item of the entry, a check box of the entry is checked using the input unit 31. By the register button 98 being selected, content of the checked nursing care record data is determined, and the content is deleted from the list. If it is determined that input of an item is insufficient, by the entry being selected using the input unit 31, the screen shifts to the nursing care record input screen as illustrated in FIG. 6 or FIG. 7. It is possible to input a value of an item, correct text data within the form, or the like, as described above on this screen. The message as illustrated in FIG. 7 may be also displayed on the shifted screen. While the text data in the form and the message are not displayed in the list in FIG. 8, at least one of these may be displayed.

Processing of the analyzer 24 in the case where there is an error in voice recognition will be described here. A form in which, in the case where there is an error in voice recognition, a correct term (keyword) is estimated will be described.

As a specific example of an error in voice recognition, there is a case where, while there is tweet of "Tohiba-sanno hainyou kakunin shimashita", the tweet is erroneously recognized as "toushi baasannno hainyou kakuninshimashita" in voice recognition. In this case, because text obtained through voice recognition does not include any name in the list of record target people, it is inferred that the user has forgot tweeting family name, name or full name of the patient or the person who is cared for, or although the user tweets the name, there is an error in voice recognition. Therefore, in such a case, a similarity between character strings may be calculated in notation of hiragana (or katakana) ("hiragana", "katakana", or "kana" is meaning of phonetic symbols in Japan), and name with the highest similarity may be selected as a candidate and may be input in an item of a record target person on the nursing care record input screen (see FIG. 6). In the case where a similarity is low, for example, in the case where a value indicating the similarity is equal to or less than a threshold (or equal to or greater than a threshold), it may be regarded as the user having forgot tweeting the name.

For example, the above-described character string including a recognition error can be expressed as "toshibaasannno hainyou" in hiragana. In the case where the family name included in the list of record target people is "toshiba", "higashi", "toushi", or the like, if a similarity with the above-described character string is calculated for each family name, because "toshiba" is the most similar, "Toshiba"-san can be estimated as an appropriate record target person. Note that it is assumed that family name, name, kana of family name, kana of name, or the like, of each record target person is stored in the list of record target people. When there are two or more record target people having the same family name, it is also possible to present a list of name of the people concerned and allow the user to select the person. While an example where name of the record target person is estimated is described here, the same also applies to a case of a term indicating an item of nursing care content (such as urination, passage and meal intake). Note that processing in the case where there is an error in voice recognition, and the above-described calculation of a similarity between character strings in hiragana will be also described in detail in the second embodiment.

Figure 9:
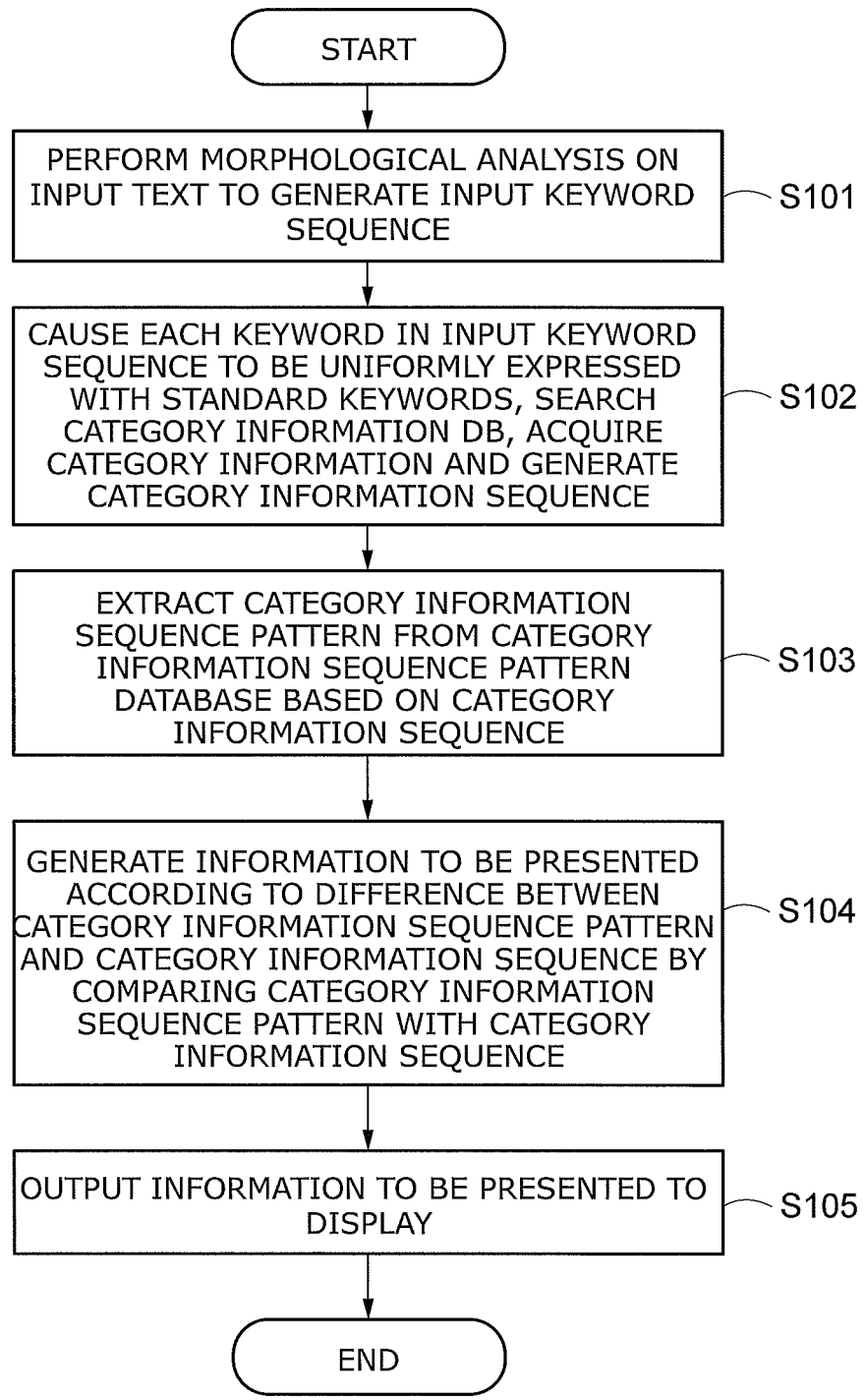
FIG. 9 is a diagram illustrating a flowchart of an operation example of an information processing device according to a first embodiment.

FIG. 9 is a flowchart illustrating an operation example of the information processing device according to the first embodiment.

(Step S101) The input processor 22 accepts input of text data in natural language from the receiver 13. The text data is held in the text data holder 23. The morphological analyzer 51 of the analyzer 24 reads out the text data from the text data holder 23 and generates a keyword sequence (input keyword sequence) including a plurality of keywords by performing morphological analysis on the text data.

(Step S102) The standard term detector 52 causes the keywords in the keyword sequence to be uniformly expressed with standard keywords based on the standard term database 61. That is, the standard term detector 52 checks whether each keyword falls under the category of a non-standard keyword, and if a keyword falls under the category of a non-standard keyword, replaces the keyword with the standard keyword. The category information generator 53 acquires category information corresponding to each keyword included in the standard keyword sequence based on the category information database 62 in which the standard keywords are associated with the category information, and generates a category information sequence.

(Step S103) The pattern extractor 54 selects a category information sequence pattern according to correlation between the category information sequence and each of a plurality of category information sequence patterns in the category information sequence pattern database 63. For example, the pattern extractor 54 calculates a similarity between the category information sequence and each of the plurality of category information sequence patterns and selects a category information sequence pattern based on the similarity. Specifically, the pattern extractor 54 selects a category information sequence pattern which satisfies a predetermined condition, such as a category information sequence pattern having the highest similarity.

(Step S104) The determiner 55 compares the selected category information sequence pattern with the category information sequence and generates presentation information according to a difference between the selected category information sequence pattern and the category information sequence. For example, as the presentation information, the determiner 55 generates information which specifies category information which is included in the category information sequence pattern and which is not included in the category information sequence. Alternatively, the determiner 55 generates a message indicating that a keyword relating to the category information is not included in the keyword sequence.

(Step S105) The output processor 26 performs control to output the presentation information to the display 41. The display 41 displays the presentation information on a screen, or the like, provided by the managing application.

As described above, according to the present embodiment, in a text obtained based on input by the user, in the case where the text lacks information of a necessary item or content of information is wrong, it is possible to detect this and promote the user to perform input.

Second Embodiment

Figure 10:
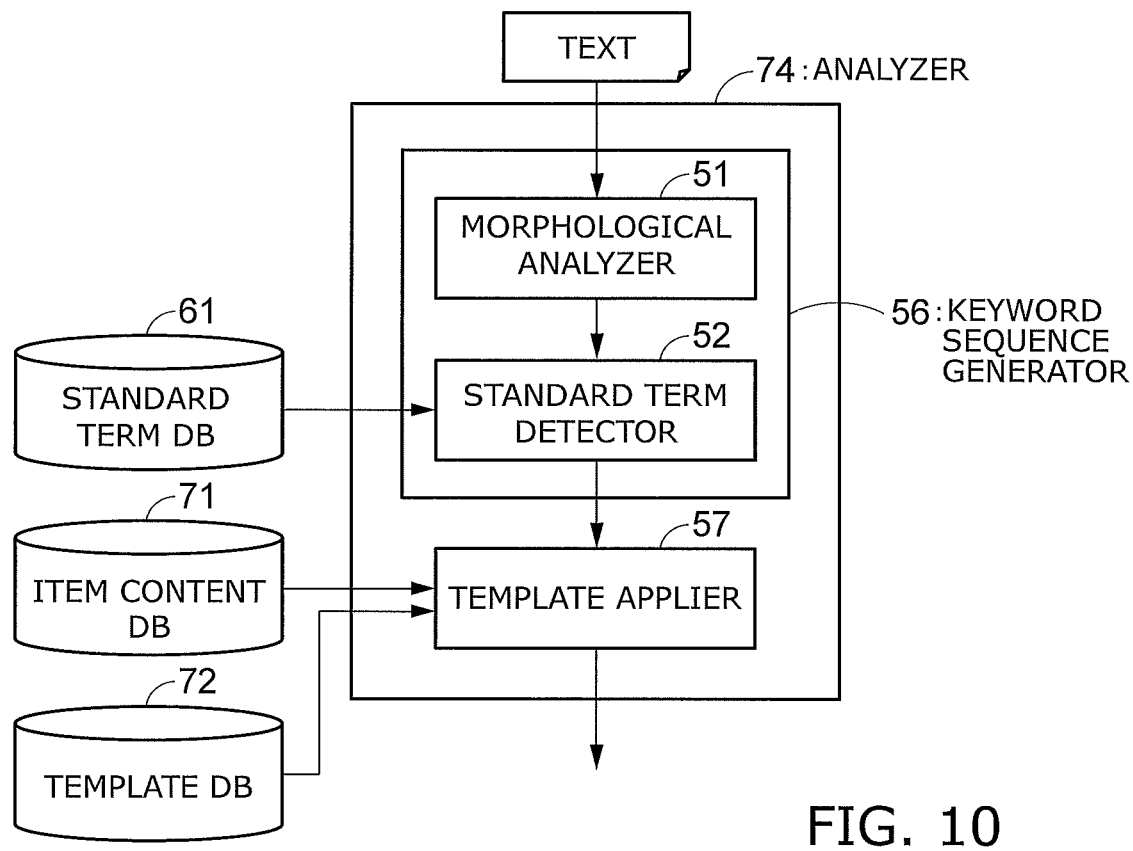
FIG. 10 is a functional block diagram of an analyzer according to a second embodiment.

The second embodiment is different from the first embodiment mainly in operation of the analyzer. The second embodiment will be described below mainly regarding operation of the analyzer. FIG. 10 is a block diagram of the analyzer according to the present embodiment. The analyzer 74 includes a morphological analyzer 51, a standard term detector 52 and a template applier 57. A standard term database 61, an item content database 71 and a template database 72 are stored in the storage 25. The morphological analyzer 51, the standard term detector 52 and the standard term database 61 are similar to those in the first embodiment.

In the present embodiment, a form will be described where, in the case where a numerical value is automatically input in an item for measurement such as vital using text data obtained through voice recognition, even in the case where there is an error in voice recognition, the numerical value can be modified with less trouble. Note that the text data may be input by the user via input means such as a keyboard as well as obtained through voice recognition.

Figure 11A:
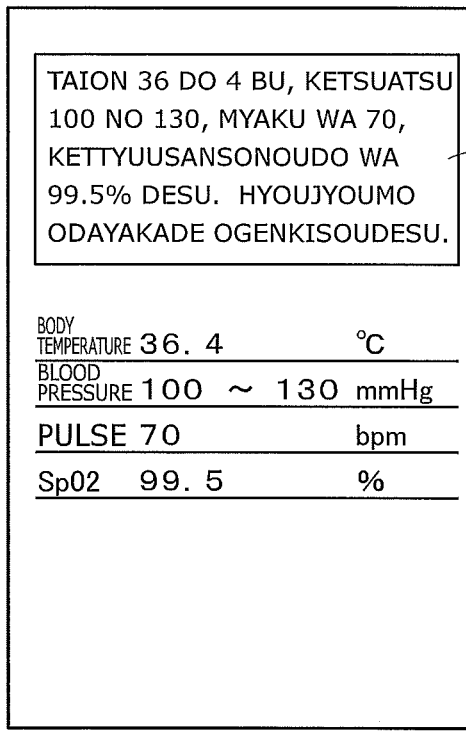
FIGS. 11A and 11B each is a diagram illustrating an example of a nursing record screen.
Figure 11B:
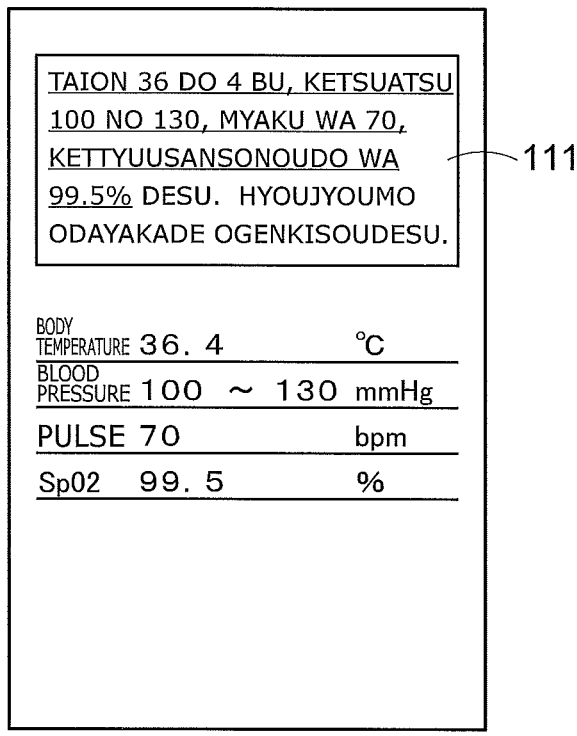

FIG. 11A is a diagram explaining outline of the present embodiment. FIG. 11A illustrates a nursing record screen. It is assumed that a text obtained through voice recognition which is stored in a form 101 is "taion 36 do 4 bu, ketsuatsu 100 no 130, myaku wa 70, kettyuusansonoudo wa 99.5% desu. Hyoujyoumo odayakasoude ogenkisoudesu". As an item relating to vital, a body temperature, a blood pressure, a pulse and Sp02 are set below the form 111. Sp02 is a blood oxygen level. A numerical value is not input in a right part of each item at first. By processing the text data according to the present embodiment, a numerical value corresponding to each item is automatically input. The example in FIG. 11A is an example where there is no error in voice recognition, and a correct numerical value is input in each item. As illustrated in FIG. 11B, it is also possible to extract an item such as vital and a numerical value from the text within the form 111 and emphasize the portions. Note that a keyword sequence is generated from the text data through morphological analysis, or the like, and it is possible to recognize correspondence between the text within the form and each keyword in the keyword sequence. Note that, while not illustrated, the nursing record screen is associated with a record target person.

In order to extract information such as a numerical value for each item from the text data or the keyword sequence, the template applier 57 uses the item content database 71 illustrated in FIG. 12A and the template database 72 illustrated in FIG. 12B. These item content database 71 and template database 72 are stored in the storage 25.

In the item content database in FIG. 12A, content, an expression form, or the like, of each item is defined. For example, in the first entry (ID_01), the item content is "taion", a unit is "° C.", and the expression form is [numerical value A]·[numerical value B]. This means that "taion: [numerical value A]·[numerical value B] ° C." is displayed on the nursing record screen. [numerical value A] and [numerical value B] indicate variables which can be arbitrary numbers, and these numerical values are extracted from the text data. The expression form is not limited to one, and as in the second entry (ID_02), a plurality of expression forms may be defined. Which expression form is applied is determined according to the extracted numerical values, and, in this example, if [numerical value A] and [numerical value B] are extracted, an expression form 1 is applied, and, if only [numerical value A] is extracted, an expression form 2 is applied.

In the template data base 72 in FIG. 12B, a template for extracting variables for each item in FIG. 12A from the text data or the keyword sequence is stored. ""in the template indicates a character string. [*N] indicates arbitrary N or less characters (instead of N or less characters, [*N] may be defined to have other meaning such as N characters). [numerical value] indicates successive numerical characters, and a symbol (A and B) added to a right part in the brackets of [numerical value] is mere a symbol for identifying a plurality of [numerical value]s.

In the first entry (ID_01) which corresponds to the first entry in FIG. 12A (item ID is common), a template for extracting [numerical value A]·[numerical value B] from the text data or the keyword sequence is stored. This template is ""taion" [*2] [numerical value A] "do" [numerical value B] "bu"". A column of extracted data 1 defines that a portion which matches the template is specified from the text data or the keyword sequence, [numerical value A] and [numerical value B] are extracted from the specified portion, and the extracted [numerical value A] and [numerical value B] are acquired in a form of "[numerical value A]·[numerical value B]". "taion 36 do 4 bu" in the text or in the portion of the corresponding keyword sequence illustrated in FIG. 11A or FIG. 11B matches this template. In this example, because the number of characters between "taion" and numerical values is zero, [*2] indicating two or less characters is satisfied. Therefore, [numerical value A] corresponds to 36, [numerical value B] corresponds to 4, and 36.4 is extracted according to a form of [numerical value A]·[numerical value B]. Then, 36.4 is displayed according to the expression form defined in the column of the expression form 1 in the item content database 71.

Further, in the third entry (ID_02), a template regarding a blood pressure of "ketsuatsu" [*3] [numerical value A] [*4] [numerical value B]" is defined. It is indicated that in the column of extracted data 1 and the column of extracted data 2, [numerical value A] and [numerical value B] are respectively defined, and extracted numerical value A and numerical value B are individually output (that is, these are not bound with ".").

If a portion which matches the template exists within the text data or the keyword sequence as with the case described above, numerical values are extracted from the portion in a similar manner, and the extracted numerical values are displayed according to the expression form defined in the column of the expression form 1 in the item content database.

In this manner, the template defines that a value located at a specific location within N characters is extracted with respect to a predetermined term such as "taion" and "ketsuatsu".

Figure 13A:
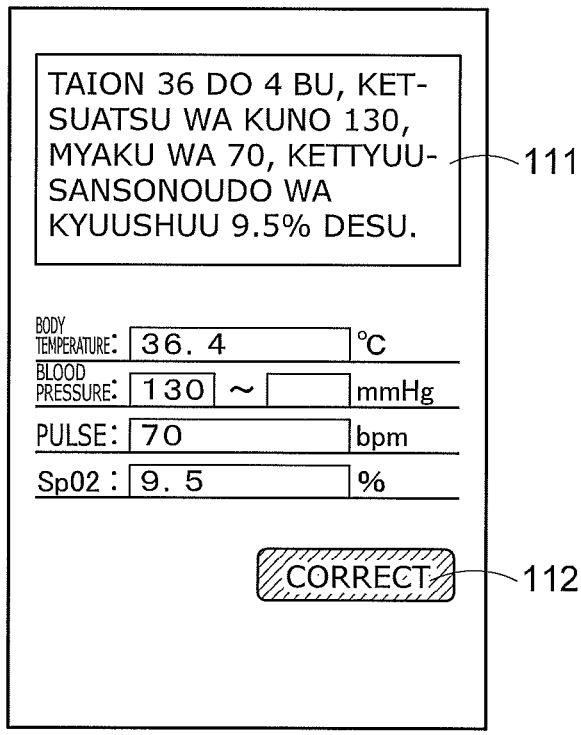
FIGS. 13A and 13B each is a diagram illustrating an example of a nursing record screen.
Figure 13B:
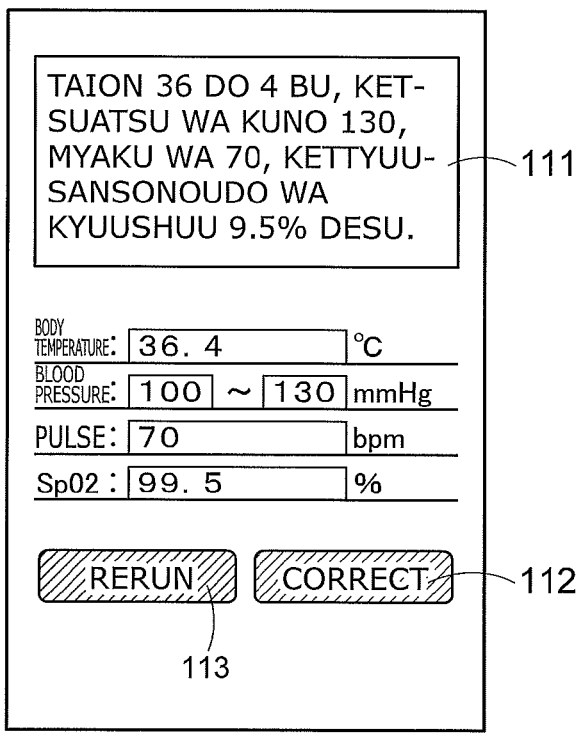

FIG. 13A is an example of the nursing record screen in the case where an error occurs in voice recognition. In this example, tweet of "ketsuatsu 100 no" is recognized as "ketsuatsu wa kuno", and tweet of "99.5" is recognized as "kyuushuu 9.5". Therefore, as a result of performing processing based on the above-described item content database and the template database, the blood pressure is displayed as "130" which should have been displayed as "100 to 130", and Sp02 is displayed as "9.5" which should have been displayed as "99.5". The user sees this result and modifies values of wrong items by inputting an instruction from the input unit 31. After modification, modified content is determined by the user selecting a correcting button 112, and data of content within the nursing record screen is stored in the storage 25, or the like, as nursing record data. At this time, when numerical values of the item are modified, the text data in the form 11 may be also modified. Alternatively, as illustrated in FIG. 13B, template application processing may be performed again by correcting the text data in the form 11 ahead and selecting a rerun button 113 for the modified text data. Also by this means, a correct value can be set in the item. FIG. 13B illustrates an example where a value wrong in FIG. 13 is corrected by performing template application processing again by correcting the text data, and, then, selecting the rerun button 113.

Figures 14, 15:
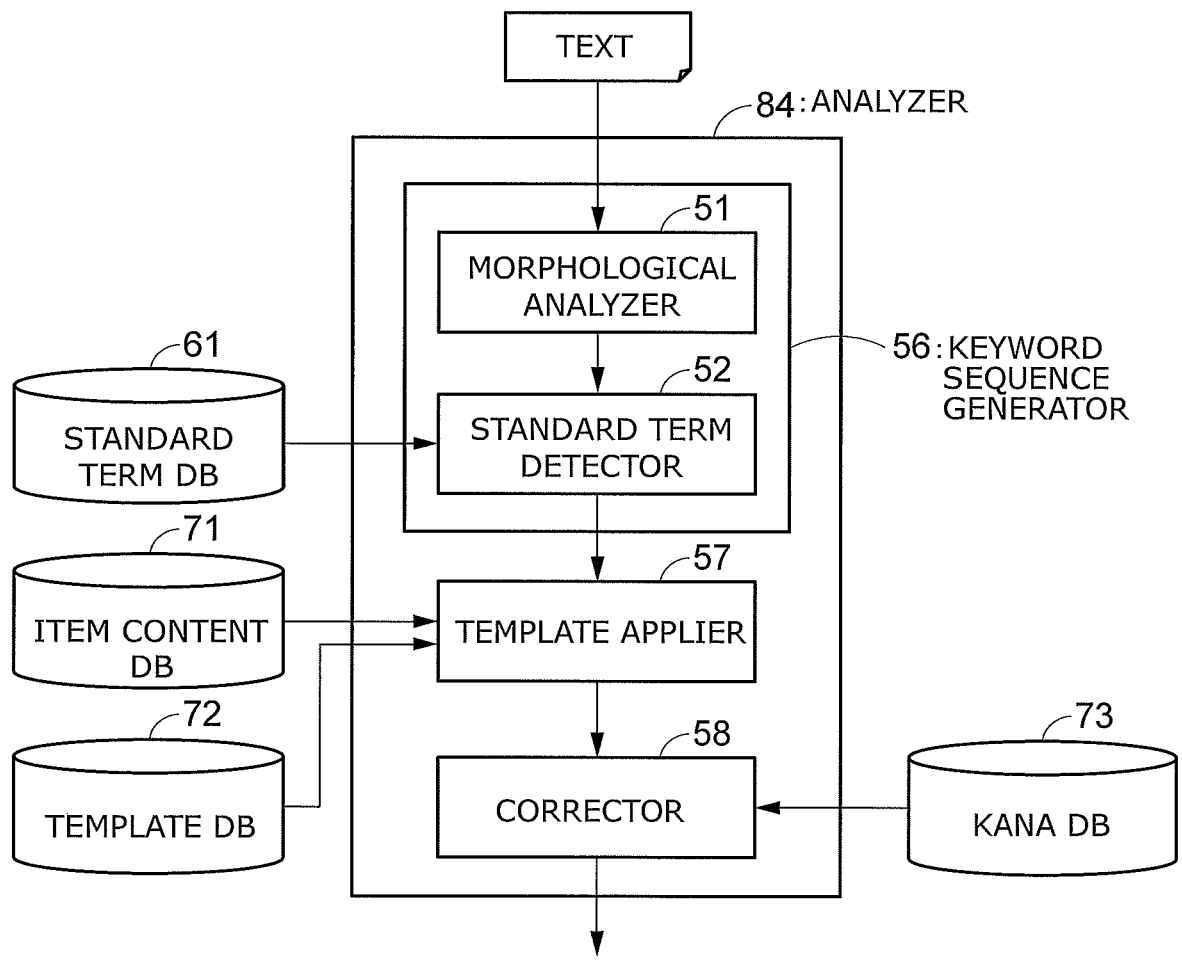
FIG. 14 is a functional block diagram of another example of the analyzer according to the second embodiment.
FIG. 15 is a diagram illustrating an example of a kana database in which a numerical value is associated with notation in hiragana of the numerical value.

While, in the example illustrated in FIG. 13A and FIG. 13B, the user modifies at least an item or a text, it is also possible to employ a form in which an error in voice recognition is automatically modified. A block diagram in this case is illustrated in FIG. 14. A corrector 54 is added after the template applier 57 in the analyzer 84. Further, a kana database 73 is stored in the storage 25.

A character string following "kettyuusansonoudo" is "wa kyuushuu 9.5%" in the text including an error in voice recognition illustrated in the form 111 in FIG. 13A, and if the corrector 58 extracts a number from this portion, "9.5" can be extracted. As the numerical value following the blood oxygen level, an appropriate range (for example, between 80 and 100) is determined in advance, and because 9.5 does not fall within this range, it is determined that it is highly likely that 9.5 is obviously an error in voice recognition. Specifically, for example, it is determined from a keyword (kettyuusansonoudo) indicating name of a measurement item located immediately before (predetermined positional relationship) a keyword of 9.5 in the keyword sequence, that a range of the value expected to be normally indicated with the keyword of 9.5 is between 80 and 100.

Therefore, as described in the first embodiment, the numerical value is modified using a similarity between character strings in hiragana. Note that other notation such as katakana and alphabet may be used instead of hiragana. An appropriate range of Sp02 (that is, a range expected as a measurement value of Sp02) is between 80 and 100, and this range is sectioned at regular intervals. Then, numerical values at respective positions at regular intervals and character strings indicating kana in hiragana are stored in the kana database 73 in association with each other. In the case where the range is between 80 and 100, and an interval is 0.1, 201 character strings can be obtained. FIG. 15 illustrates an example of the kana database 73. Numbers (keywords) from 80.0 to 100.0 at intervals of 0.1 and character strings indicating kana of the respective numbers (keywords) in hiragana are set in association with each other. Kana for one numerical value is not limited to one, and a plurality of kanas may be set for one numerical value.

A portion where it is determined as the above-described error in voice recognition is specified. For example, a character string from the character following "kettyuusansonoudo" to the numerical value determined as the above-described error is specified as the portion where it is determined as the error in voice recognition. Specifically, a character string including a keyword (one or more successive keywords) from a keyword subsequent to "kettyuusansonoudo" to 9.5 which is determined as an error in voice recognition is specified. The specified portion is converted into kana notation in hiragana, and a similarity with each hiragana character string in the kana database 73 is calculated. In the right column of the kana database 73 in FIG. 15, similarities calculated this time are stored. Note that a column in which the similarity is stored does not have to be provided. In the case where a plurality of types of kana are set for one numerical value, it is only necessary to employ kana with the highest similarity. The highest similarity is 97 this time, and a character string with this similarity is "kyujyuukyuutenngo (99.5)". Therefore, the corrector 58 modifies the value 9.5 in the item of Sp02 in FIG. 13A with the specified 99.5. Note that while, in the example in FIG. 15, the similarity becomes higher as the value becomes greater, there is a case where the similarity becomes higher as the value becomes smaller depending on the calculation method.

As described at the end of the description of the first embodiment, processing of absorbing (correcting) an error in voice recognition in the second embodiment may be applied to the first embodiment. Further, it is also possible to apply the processing of absorbing an error in voice recognition to a case where each keyword in the keyword sequence is standardized (uniformly expressed with standard keywords). For example, in the case where a keyword in the keyword sequence is neither a standard keyword nor registered as a non-standard keyword in the standard term database 61, the keyword is converted into hiragana notation. A database in which standard keywords are associated with kana in hiragana is prepared in a storage which can be accessed by the standard term detector 52, a similarity between each hiragana notation in the database and the keyword is calculated. A standard keyword corresponding to kana with the highest similarity and equal to or higher than a threshold is employed as a standard keyword of the keyword. By this means, it is possible to absorb an error in voice recognition also when terms are standardized, so that it is possible to appropriately proceed with the subsequent processing (for example, acquire an appropriate category information sequence in the first embodiment and improve extraction accuracy of the category information sequence pattern).

The second embodiment can be combined with the first embodiment. In this case, it is only necessary to respectively provide functions necessary in both the first and the second embodiments to the analyzer and the storage.

As described above, according to the present embodiment, in the case where a numerical value such as vital is input using tweeting and the numerical value is recognized as a value or characters different from the numerical value due to an error in voice recognition, it is possible to correct the error with less trouble or automatically.

Third Embodiment

Figure 16:
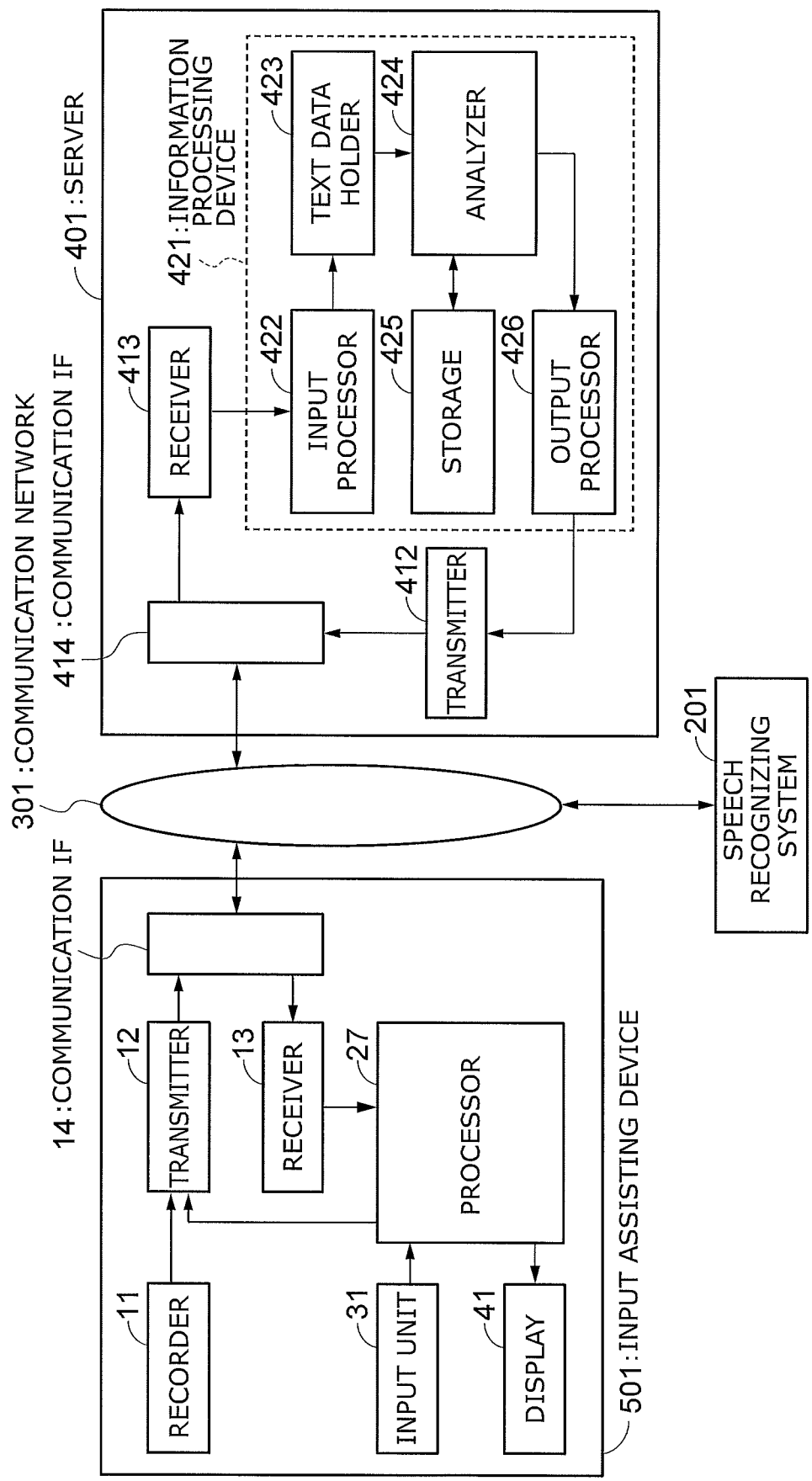
FIG. 16 is a diagram of a system configuration in which an information processing device according to a third embodiment is mounted on a server.

While, in the first and the second embodiments, the information processing device is implemented in a user terminal (input assisting device), it is also possible to provide functions of the information processing device in a server on a communication network. FIG. 16 illustrates a system configuration in which the information processing device according to the present embodiment is mounted on a server on a communication network.

The input assisting device 501 includes a processor 27 in place of the analyzer in the first embodiment. The processor 27 receives the text data obtained through voice recognition in the voice recognition system 201 from the receiver 13 and transmits a request for analysis processing of the text data to a server 401.

The server 401 includes a communication interface 414, a receiver 413, a transmitter 412 and an information processing device 421. The information processing device 421 includes an input processor 422, a text data holder 423, an analyzer 424, a storage 425 and an output processor 426. Each function of these units are similar to that of components having the same name in the input assisting device in the first and the second embodiments, except that the output processor 426 transmits the analysis result of the analyzer 424 to the input assisting device 501 via the transmitter 412.

The processor 27 of the input assisting device 101 receives the analysis result transmitted from the server 401 via the receiver 13 and displays the analysis result at the display 41. In the case where various kinds of instructions or data is input from the user via the input unit 31, the instructions or data is transmitted to the server 401 via the transmitter 12.

The server 401 passes the instructions or data received from the input assisting device 501 to the information processor 421 via the receiver 413.

In this manner, by providing basic functions of the information processing device in the first and the second embodiments at the server 401 side, it is possible to reduce load and storage capacity of the input assisting device 501. Note that the server 401 can also respectively processing requests from a plurality of input assisting devices. The voice recognition system 201 may be integrated with the server 401, or the voice recognition system 201 may be provided within the input assisting device 501.

The information processing device or the input assisting device in each embodiment may also be realized using a general-purpose computer device as basic hardware. That is, each function provided in The information processing device or the input assisting device can be realized by causing a processor mounted in the above described computer device to execute a program. In this case, the information processing device or a management server may be realized by installing the above described program in the computer device beforehand or may be realized by storing the program in a storage medium such as a CD-ROM or distributing the above described program over a network and installing this program in the computer device as appropriate. Furthermore, the storages provided in the information processing device or the input assisting device may also be realized using a memory device or hard disk incorporated in or externally added to the above described computer device or a storage medium such as CD-R, CD-RW, DVD-RAM, DVD-R as appropriate.

A "processor" may encompass a general purpose processor, a central processing unit (CPU), a microprocessor, a digital signal processor (DSP), a controller, a microcontroller, a state machine, and so on. According to circumstances, a "processor" may refer to an application specific integrated circuit (ASIC), a field programmable gate array (FPGA), and a programmable logic device (PLD), etc. The "processor" may refer to a combination of processing devices such as a plurality of microprocessors, a combination of a DSP and a microprocessor, or one or more microprocessors in conjunction with a DSP core.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions.

REFERENCE SIGNS LIST

101 INPUT ASSISTING DEVICE
201 VOICE RECOGNITION SYSTEM
301 COMMUNICATION NETWORK
11 RECORDER (VOICE RECORDER)
12, 412 TRANSMITTER
13, 413 RECEIVER
14, 414 COMMUNICATION INTERFACE (IF)
21, 421 INFORMATION PROCESSING DEVICE
31 INPUT UNIT

41 DISPLAY
22, 422 INPUT PROCESSOR
23, 423 TEXT DATA HOLDER
24, 424 ANALYZER
25, 425 STORAGE
26, 426 OUTPUT PROCESSOR
51 MORPHOLOGICAL ANALYZER
52 STANDARD TERM DETECTOR
53 CATEGORY INFORMATION SEQUENCE GENERATOR
54 PATTERN EXTRACTOR
57 TEMPLATE APPLIER
58 CORRECTOR
61 STANDARD TERM DATABASE
62 CATEGORY INFORMATION DATABASE
63 CATEGORY INFORMATION SEQUENCE DATABASE
71 ITEM CONTENT DATABASE
72 TEMPLATE DATABASE
73 KANA DATABASE

The invention claimed is:

1. An information processing device comprising one or more computer processors configured to:
generate a keyword sequence by performing morphological analysis on text data in natural language wherein the text data is obtained by performing voice recognition processing on data indicating speech content by a user wherein the speech content is relating to a patient or a person who is cared for;
based on a database including keywords and category information associated therewith, acquire category information corresponding to each keyword of the keyword sequence to generate a category information sequence;
select a category information sequence pattern from a plurality of category information sequence patterns according to correlation between the category information sequence and each category information sequence pattern;
compare the selected category information sequence pattern with the category information sequence and generate presentation information according to a difference between the selected category information sequence pattern and the category information sequence;
output an input screen including a field for input of a value associated with a predetermined state of the patient or the person who is cared for, to a display device;
detect a keyword matching a term expressing the predetermined state from the keyword sequence, and based on a template associating the term with a position condition, extract a keyword located at a position satisfying the position condition for the detected keyword, from the keyword sequence, and
set the extracted keyword in the field of the input screen as the value associated with the predetermined state.

2. The information processing device according to claim 1, wherein the one or more computer processors are configured to:
output the presentation information to the display device.

3. The information processing device according to claim 1, wherein the one or more computer processors are configured to:
calculate a similarity between the category information sequence and each of the plurality of category information sequence patterns and select the category information sequence pattern based on the similarity.

4. The information processing device according to claim 1,
wherein the presentation information specifies category information which is included in the selected category information sequence pattern and which is not included in the category information sequence.

5. The information processing device according to claim 1,
wherein the presentation information includes a message notifying that a keyword relating to category information which is included in the selected category information sequence pattern and which is not included in the category information sequence is not included in the keyword sequence.

6. The information processing device according to claim 1, wherein the one or more computer processors are configured to:
detect a keyword relating to an input item on an input screen from the keyword sequence, and set information depending on the detected keyword as a value of the input item.

7. The information processing device according to claim 1, wherein the one or more computer processors are configured to:
determine whether the keyword included in the keyword sequence corresponds to a non-standard keyword based on a standard term database having standard keywords and the non-standard keyword associated therewith, and, in the case where the keyword corresponds to the non-standard keyword, replace the keyword in the keyword sequence with the standard keyword associated with the keyword.

8. The information processing device according to claim 1, wherein the one or more computer processors are configured to:
convert a character string including one or more successive keywords detected in the keyword sequence into first notation indicating phonetic symbols of the character string,
specify, based on a database having a plurality of keywords and second notation indicating phonetic symbols of each of the plurality of keywords, one keyword among the plurality of keywords in the database based on correlation between the first notation and the second notation of each of the plurality of keywords, and
replace the character string in the keyword sequence with the specified one keyword or replace a portion corresponding to the character string in the text data with the specified one keyword.

9. The information processing device according to claim 8, wherein the one or more computer processors are configured to:
specify a range of a value expected to be indicated by a first keyword in the keyword sequence based on a second keyword which has predetermined positional relationship with the first keyword, and,
when a value indicated by the first keyword does not fall within the range, detect a character string including one or more successive keywords including the first keyword from the keyword sequence.

10. The information processing device according to claim 9,
wherein the second keyword indicates a term of an item relating to measurement, and the range of the value expected to be indicated by the first keyword is a range of a measurement value which is expected to be obtained by the measurement.

11. An information processing device according to claim 1, wherein
the position condition specifies a position after a predetermined number of characters after the keyword matching the term in the keyword sequence.

12. An information processing device according to claim 1, wherein
the position condition specifies to extract a numeral value from within a predetermined number of characters after the keyword matching the term in the keyword sequence.

13. An information processing method performed by a computer, comprising:
generating a keyword sequence by performing morphological analysis on text data in natural language wherein the text data is obtained by performing voice recognition processing on data indicating speech content by a user wherein the speech content is relating to a patient or a person who is cared for;
acquiring, based on a database including keywords and category information associated therewith, category information corresponding to each keyword of the keyword sequence and generates a category information sequence;
selecting a category information sequence pattern from a plurality of category information sequence patterns according to correlation between the category information sequence and each category information sequence pattern;
comparing the selected category information sequence pattern with the category information sequence and generates presentation information according to a difference between the selected category information sequence pattern and the category information sequence;
outputting an input screen including a field for input of a value associated with a predetermined state of the patient or the person who is cared for, to a display device;
detecting a keyword matching a term expressing the predetermined state from the keyword sequence, and based on a template associating the term with a position condition, extracts a keyword located at a position satisfying the position condition for the detected keyword, from the keyword sequence; and
setting the extracted keyword in the field of the input screen as the value associated with the predetermined state.

14. A non-transitory computer readable medium having a computer program stored therein which, when the computer program is executed by a computer, causes the computer to perform processes comprising:
generating a keyword sequence by performing morphological analysis on text data in natural language wherein the text data is obtained by performing voice recognition processing on data indicating speech content by a user wherein the speech content is relating to a patient or a person who is cared for;
acquiring, based on a database including keywords and category information associated therewith, category information corresponding to each of a plurality of keywords included in the keyword sequence and generates a category information sequence;
selecting a category information sequence pattern from a plurality of category information sequence patterns according to correlation between the category information sequence and each category information sequence pattern;
comparing the selected category information sequence pattern with the category information sequence and generates presentation information according to a difference between the selected category information sequence pattern and the category information sequence;
outputting an input screen including a field for input of a value associated with a predetermined state of the patient or the person who is cared for, to a display device;
detecting a keyword matching a term expressing the predetermined state from the keyword sequence, and based on a template associating the term with a position condition, extracts a keyword located at a position satisfying the position condition for the detected keyword, from the keyword sequence; and
setting the extracted keyword in the field of the input screen as the value associated with the predetermined state.

15. An information processing device comprising one or more computer processors configured to:
generate a keyword sequence by performing morphological analysis on text data in natural language;
based on a database including keywords and category information associated therewith, acquire category information corresponding to each keyword of the keyword sequence to generate a category information sequence;
select a category information sequence pattern from a plurality of category information sequence patterns according to correlation between the category information sequence and each category information sequence pattern;
compare the selected category information sequence pattern with the category information sequence and generates presentation information according to a difference between the selected category information sequence pattern and the category information sequence;
convert a character string including one or more successive keywords detected in the keyword sequence into first notation indicating phonetic symbols of the character string;
specify, based on a database having a plurality of keywords and second notation indicating phonetic symbols of each of the plurality of keywords, one keyword among the plurality of keywords in the database based on correlation between the first notation and the second notation of each of the plurality of keywords;
replace the character string in the keyword sequence with the specified one keyword or replace a portion corresponding to the character string in the text data with the specified one keyword;
specify a range of a value expected to be indicated by a first keyword in the keyword sequence based on a second keyword which has predetermined positional relationship with the first keyword, and
when a value indicated by the first keyword does not fall within the range, detect a character string including one or more successive keywords including the first keyword from the keyword sequence.

16. An information processing method performed by a computer, comprising:

generating a keyword sequence by performing morphological analysis on text data in natural language;
acquiring, based on a database including keywords and category information associated therewith, acquires category information corresponding to each keyword of the keyword sequence to generate a category information sequence;
selecting a category information sequence pattern from a plurality of category information sequence patterns according to correlation between the category information sequence and each category information sequence pattern;
comparing the selected category information sequence pattern with the category information sequence and generating presentation information according to a difference between the selected category information sequence pattern and the category information sequence;
converting a character string including one or more successive keywords detected in the keyword sequence into first notation indicating phonetic symbols of the character string;
specifying, based on a database having a plurality of keywords and second notation indicating phonetic symbols of each of the plurality of keywords, one keyword among the plurality of keywords in the database based on correlation between the first notation and the second notation of each of the plurality of keywords;
replacing the character string in the keyword sequence with the specified one keyword or replace a portion corresponding to the character string in the text data with the specified one keyword; and
specifying a range of a value expected to be indicated by a first keyword in the keyword sequence based on a second keyword which has predetermined positional relationship with the first keyword,
when a value indicated by the first keyword does not fall within the range, detecting a character string including one or more successive keywords including the first keyword from the keyword sequence.

17. A non-transitory computer readable medium having a computer program stored therein which, when the computer program is executed by a computer, causes the computer to perform processes comprising:
generating a keyword sequence by performing morphological analysis on text data in natural language;
acquiring, based on a database including keywords and category information associated therewith, acquires category information corresponding to each keyword of the keyword sequence to generate a category information sequence;
selecting a category information sequence pattern from a plurality of category information sequence patterns according to correlation between the category information sequence and each category information sequence pattern;
comparing the selected category information sequence pattern with the category information sequence and generating presentation information according to a difference between the selected category information sequence pattern and the category information sequence;
converting a character string including one or more successive keywords detected in the keyword sequence into first notation indicating phonetic symbols of the character string;
specifying, based on a database having a plurality of keywords and second notation indicating phonetic symbols of each of the plurality of keywords, one keyword among the plurality of keywords in the database based on correlation between the first notation and the second notation of each of the plurality of keywords;
replacing the character string in the keyword sequence with the specified one keyword or replace a portion corresponding to the character string in the text data with the specified one keyword; and
specifying a range of a value expected to be indicated by a first keyword in the keyword sequence based on a second keyword which has predetermined positional relationship with the first keyword,
when a value indicated by the first keyword does not fall within the range, detecting a character string including one or more successive keywords including the first keyword from the keyword sequence.

* * * * *